(12) United States Patent
Chen et al.

(10) Patent No.: US 9,310,332 B2
(45) Date of Patent: Apr. 12, 2016

(54) SEMICONDUCTOR DEVICE AND SELECTIVE HEATING THEREOF

(71) Applicant: Taiwan Semiconductor Manufacturing Company Limited, Hsin-Chu (TW)

(72) Inventors: Tung-Tsun Chen, Hsinchu (TW); Jui-Cheng Huang, Hsinchu (TW); Chin-Hua Wen, Toufen Township (TW); Chun-wen Hung Cheng, Zhubei (TW); Yi-Shao Jonathan Liu, Zhubei (TW)

(73) Assignee: Taiwan Semiconductor Manufacturing Company Limited, Hsin-Chu (TW)

( * ) Notice: Subject to any disclaimer, the term of this patent is extended or adjusted under 35 U.S.C. 154(b) by 46 days.

(21) Appl. No.: 14/079,703

(22) Filed: Nov. 14, 2013

(65) Prior Publication Data

US 2015/0129937 A1 May 14, 2015

(51) Int. Cl.
*G01N 27/403* (2006.01)
*G01N 27/414* (2006.01)
*H01L 23/34* (2006.01)
*H01L 29/66* (2006.01)

(52) U.S. Cl.
CPC .......... *G01N 27/4145* (2013.01); *H01L 23/345* (2013.01); *H01L 29/66477* (2013.01); *H01L 2924/0002* (2013.01)

(58) Field of Classification Search
CPC . G01N 27/414; G01N 27/128; G01N 27/227; G01N 27/4148; G01N 27/4145; G01N 33/0031; H01L 21/00; H01L 21/02; H01L 21/02019; H01L 21/02008; H01L 29/66477; H01L 23/345; B82Y 15/00; B82Y 35/00

USPC .......... 257/253, E29.242; 204/400, 403, 408, 204/411, 412, 415, 416, 192.22, 192.23, 204/192.25; 422/82.01, 82.02, 82.03, 83, 422/98; 435/287.5, 91.2, 91.5, 197; 438/197, 311; 506/2, 20, 38
See application file for complete search history.

(56) References Cited

U.S. PATENT DOCUMENTS

| 6,203,683 | B1 * | 3/2001 | Austin et al. .................. 204/547 |
| 6,573,741 | B2 * | 6/2003 | Chou et al. ............... 324/750.08 |
| 8,821,798 | B2 * | 9/2014 | Bustillo ................ B01L 3/5027 204/192.25 |

(Continued)

OTHER PUBLICATIONS

"An Integrated ISFET Sensor Array", Kazuo Nakazato, Nov. 4, 2009, Sensors 2009, 9, ISSN 1424-8220, pp. 8831-8851.

(Continued)

*Primary Examiner* — Tuan Nguyen
(74) *Attorney, Agent, or Firm* — Cooper Legal Group, LLC

(57) ABSTRACT

One or more semiconductor devices and array arrangements and methods of formation are provided. A semiconductor device includes an ion sensing device and a heating element proximate the ion sensing device. The ion sensing device has an active region, including a source, a drain, and a channel, the channel situated between the source and the drain. The ion sensing device also has an ion sensing film situated over the channel, and an ion sensing region over the ion sensing film. Responsive to a temperature sensed by a thermal sensor proximate the ion sensing device, the heating element is selectively activated to alter a temperature of the ion sensing region to promote desired operation of the semiconductor device, such as to function as a bio sensor. Multiple semiconductor devices can be formed into an array.

20 Claims, 7 Drawing Sheets

(56) References Cited

U.S. PATENT DOCUMENTS

| | | | | |
|---|---|---|---|---|
| 8,945,912 | B2* | 2/2015 | Bashir | B82Y 15/00 422/82.01 |
| 2004/0238379 | A1* | 12/2004 | Lindsay et al. | 205/792 |
| 2006/0035400 | A1* | 2/2006 | Wu | H01L 27/14692 438/49 |
| 2008/0280776 | A1* | 11/2008 | Bashir et al. | 506/9 |
| 2011/0208457 | A1* | 8/2011 | Merz | G01N 27/4148 702/65 |

OTHER PUBLICATIONS

"An electronic DNA Sensor Chip using Integrated Capacitive Readout Circuit", Byunghun Lee, Kang-Ho Lee, Jeong-Oen Lee, Mi-Jin Sohn, Suk-Hwan Choi, Se-Won Wang, Jun-Bo Yoon and Gyu-Hyeong Cho, Aug. 31-Sep. 4, 2010, 32nd Annual International Conference of the IEEE EMSS, Buenos Aires, Argentina, pp. 6547-6550.

"CMOS Capacitive Biosensor with Enhanced Sensitivity for Label-Free DNA Detection", Kang-Ho Lee, Sukhwan Choi, Jeong Oen Lee, Jun-Bo Yoon and Gyu-Hyeong Cho, 2012, IEEE International Solid-Stat4 Circuits Conference, ISSCC 2012, Session 6, Medical, Displays and Imagers, 6.6, 3 pgs.

"Label-Free CMOS Bio Sensor with On-Chip Noise Reductin Scheme for Real-Time Quantitative Monitoring of Biomolecules", Seong-Jin Kim and Euisik Yoon, Jun. 2012, IEEE Transactions on Biomedical Circuits and Systems, vol. 6, No. 3, pp. 189-196.

"Silicon Nanowire field-Effect Transistor-Based Biosensors for Biomedical Diagnosis and Cellular Recording Investigation", Kuan-I-Chen, Bor-Ran Li and Yit-Tsong Chen, Feb. 2011, Nano Today (2011) 6, pp. 131-154.

Shinsuke Tanaka, Ayahito Uetake, Susumu Yamazaki, Mitsuru Ekawa, and Ken Morito, "Output Level Control of SOA Using On-Chip Heater for High Output Operation." Journal of Lightwave Technology, vol. 28, No. 17, Sep. 1, 2010, p. 2477.

V.P. Iordanov, J. Bastemeijer, A. Bossche, P.M. Sarro, M. Malatek, I.T. Young, G.W.K. van Dedem, M.J. Vellekoop, "PCR Array and Chip-Thermal Characterization." Electron. Instrument Lab., Delft University of Technology, Netherlands, In proceeding of: Sensors, 2003. Propceedings of IEEE, vol. 2. Nov. 2003, p. 1045.

* cited by examiner

SEMICONDUCTOR DEVICE AND SELECTIVE HEATING THEREOF

BACKGROUND

In a semiconductor device, current flows through a channel region between a source region and a drain region upon application of a sufficient voltage or bias to a gate of the device. When current flows through the channel region, the device is generally regarded as being in an 'on' state, and when current is not flowing through the channel region, the device is generally regarded as being in an 'off' state.

DESCRIPTION OF THE DRAWINGS

Aspects of the disclosure are understood from the following detailed description when read with the accompanying drawings. It will be appreciated that elements and/or structures of the drawings are not necessarily be drawn to scale. Accordingly, the dimensions of the various features may be arbitrarily increased and/or reduced for clarity of discussion.

DETAILED DESCRIPTION

Figure 1:
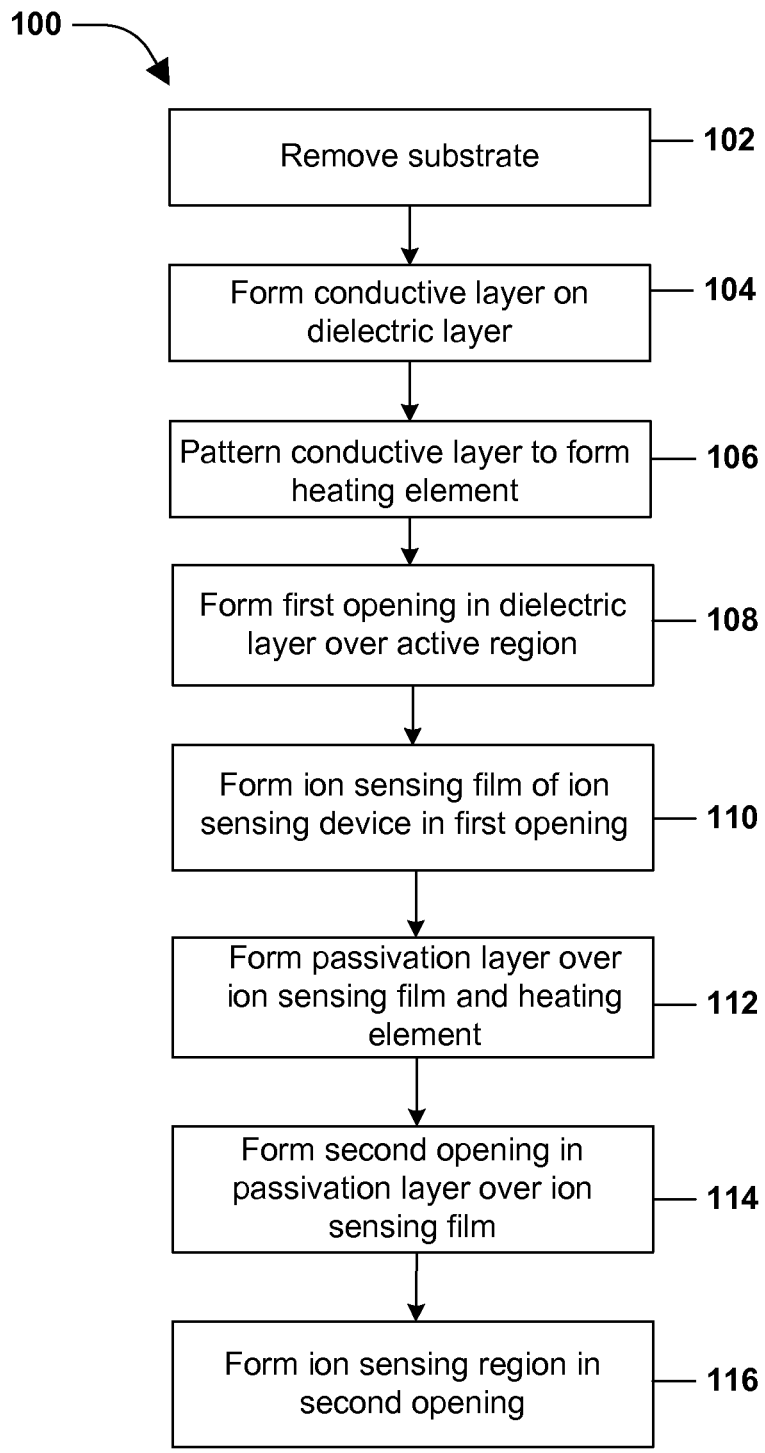
FIG. 1 is a flow diagram illustrating a method of forming a semiconductor device comprising an ion sensing device and heating element, according to some embodiments.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It is evident, however, that the claimed subject matter may be practiced without these specific details. In other instances, structures and devices are illustrated in block diagram form in order to facilitate describing the claimed subject matter.

A semiconductor device comprising an active region and a heating element proximate the active region, as provided herein, is useful for various purposes, such as for sensing bio materials. In some embodiments, the active region comprises a source, a drain, and a channel situated between the source and the drain. In some embodiments, an ion sensing film is situated over the channel. In some embodiments, an ion sensing region is situated over the ion sensing film. In some embodiments, the ion sensing region contains a liquid. In some embodiments, the heating element alters a temperature in the ion sensing region in response to applied current, or a current flowing through the heating element. In some embodiments, the heating element comprises a resistor. In some embodiments, the semiconductor device maintains a first temperature in the ion sensing region. In some embodiments, the semiconductor device maintains a second temperature in the ion sensing region. In some embodiments, the semiconductor device switches from the first temperature in the ion sensing region to the second temperature in the ion sensing region. In some embodiments, the semiconductor device maintains a third temperature in the ion sensing region. In some embodiments, the semiconductor device switches from the second temperature in the ion sensing region to the third temperature in the ion sensing region. In some embodiments, the semiconductor device switches from the third temperature in the ion sensing region to the first temperature in the ion sensing region. In some embodiments, the first temperature is between about 90 degrees C. to about 100 degrees C. In some embodiments, the second temperature is between about 20 degrees C. to about 70 degrees C. In some embodiments, the third temperature is between about 65 degrees C. to about 80 degrees C. In some embodiments, the semiconductor device comprises a thermal sensor that measures a local temperature. In some embodiments, the thermal sensor is proximate at least one of the ion sensing region or the active region to measure a temperature thereof. In some embodiments, the thermal sensor thus signals the heating element to affect a switch between at least one of the first temperature, the second temperature or the third temperature. At least one of the ion sensing region or the ion sensing film generally function as a gate of a transistor that comprises the source, the drain and the channel such that current will or will not flow through the channel between the source and the drain depending upon a material in or a composition of the ion sensing region. In some embodiments, the semiconductor device is configured to sense an ion, such as within a buffer liquid in the ion sensing region. In some embodiments, the semiconductor device is configured to sense charge which is bound or linked to a molecule or a bio-molecule, such as a DNA base pair, such as where the molecule or the bio-molecule are within a buffer liquid in the ion sensing region. The temperature of at least one of the ion sensing region or the active region also influences the operation of the transistor. Accordingly, selective activation of the heating element, as a function of a temperature measured by the thermal sensor, promotes desired operation of the semiconductor device, such as to function as a bio sensor.

One or more arrangements of a semiconductor device are provided herein. In some embodiments, a heating element of the semiconductor device is formed after an active region of the semiconductor device is formed. In some embodiments, the heating element is formed during the formation of the active region.

Figure 2:
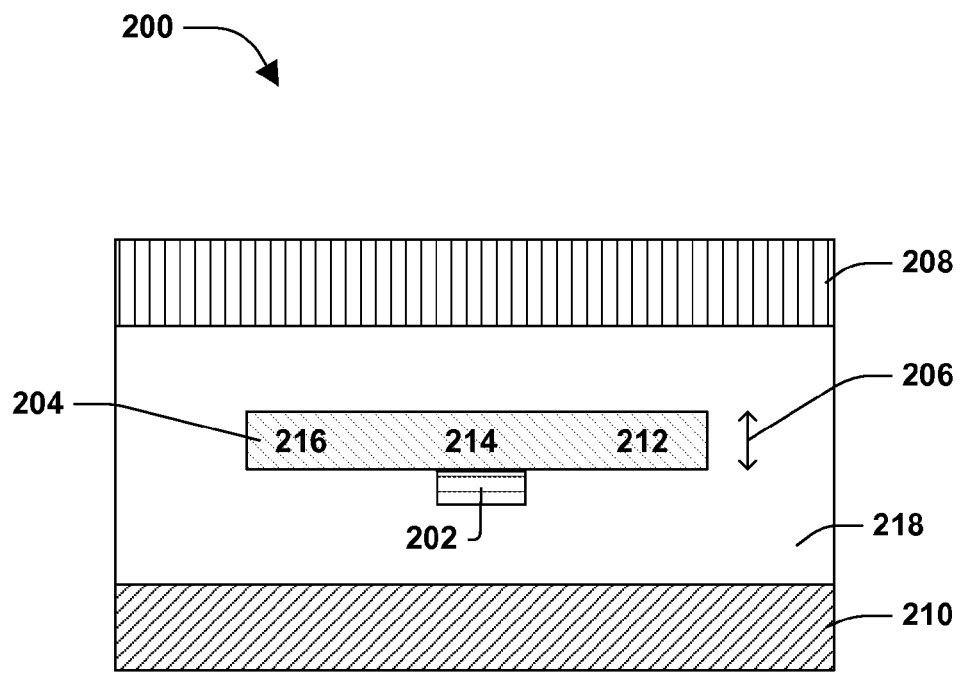
FIG. 2 is an illustration of a semiconductor device, according to some embodiments.

A method 100 of forming a semiconductor device 200 having an ion sensing device 234 and heating element 222 is illustrated in FIG. 1, and one or more semiconductor arrangements formed by such a methodology are illustrated in FIGS. 2-8. A semiconductor arrangement includes an active region 204 and a gate 202 embedded in a dielectric layer 218, as illustrated in FIG. 2. In some embodiments, the dielectric layer 218 is deposited. In some embodiments, the dielectric layer 218 is grown. In some embodiments, the dielectric layer 218 comprises a thickness of between about 0.5 µm to about 20 µm. In some embodiments, the dielectric layer 218 comprises at least one of silicon oxide ($SiO_2$) or silicon nitride (Si$_3$N$_4$). The dielectric layer 218 comprising the active region 204 and the gate 202 is formed on a first substrate 208 and is inverted and placed on a handle substrate 210. In some embodiments, the first substrate 208 comprises an epitaxial layer, a silicon-on-insulator (SOI) structure, a wafer, or a die formed from a wafer. In some embodiments, the handle substrate 210 is made of at least one of silicon or glass. In some embodiments, the handle substrate 210 comprises a thickness of between about 50 μm to about 500 μm. In some embodiments, the active region 204 comprises a source 212, a drain 216, and a channel 214. The channel 214 is situated between the source 212 and drain 216, and above the gate 202. In some embodiments, the gate 202 is adjacent the active region 204 diametrically opposite an ion sensing film 224, illustrated in FIG. 5, relative to the channel 214. In some embodiments, the gate 202 comprises at least one of polysilicon or metal. In some embodiments, the active region 204 comprises a nanowire, such as where a contact is connected to the source 212 and the drain 216 but is not connected to the gate 202. In some embodiments, the active region 204 and the gate 202 comprise one of a MOSFET or an ion sensing FET. In some embodiments, the active region 204 comprises a thickness 206 of between about 0.05 μm to about 5 μm. In some embodiments, the active region 204 is formed in a thermal electric isolation layer. In some embodiments, the thermal isolation layer comprises at least one of a shallow trench isolation layer or an interlayer dielectric. In some embodiments, the thermal isolation layer comprises SiO$_2$. In some embodiments, the thermal isolation layer comprises a thickness of between about 0.05 μm to about 5 μm or a thickness equal to or substantially equal to the thickness 206 of the active region 204.

At 102, the first substrate 208 is removed, as illustrated in FIG. 2. In some embodiments, the first substrate is removed by one of etching or chemical mechanical polishing (CMP).

Figure 3:
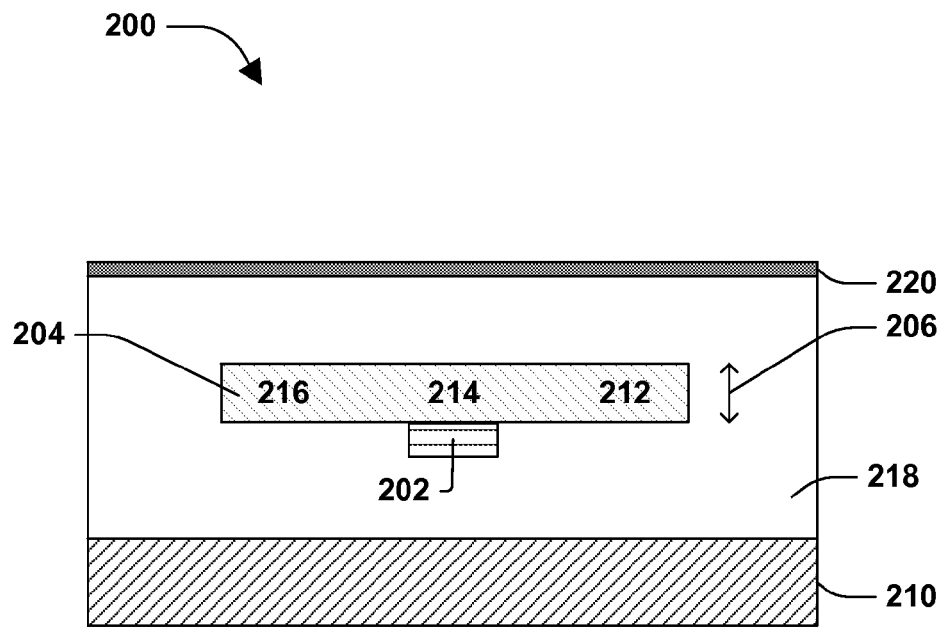
FIG. 3 is an illustration of a semiconductor device, according to some embodiments.

At 104, a conductive layer 220 is formed over the dielectric layer 218, as illustrated in FIG. 3. In some embodiments, the conductive layer 220 comprises a metal. In some embodiments, the conductive layer 220 comprises at least one of aluminum, copper, or polysilicone. In some embodiments, the metal is deposited to form the conductive layer 220. In some embodiments, the conductive layer 220 comprises a thickness of between about 0.05 μm to about 5 μm.

Figure 4:
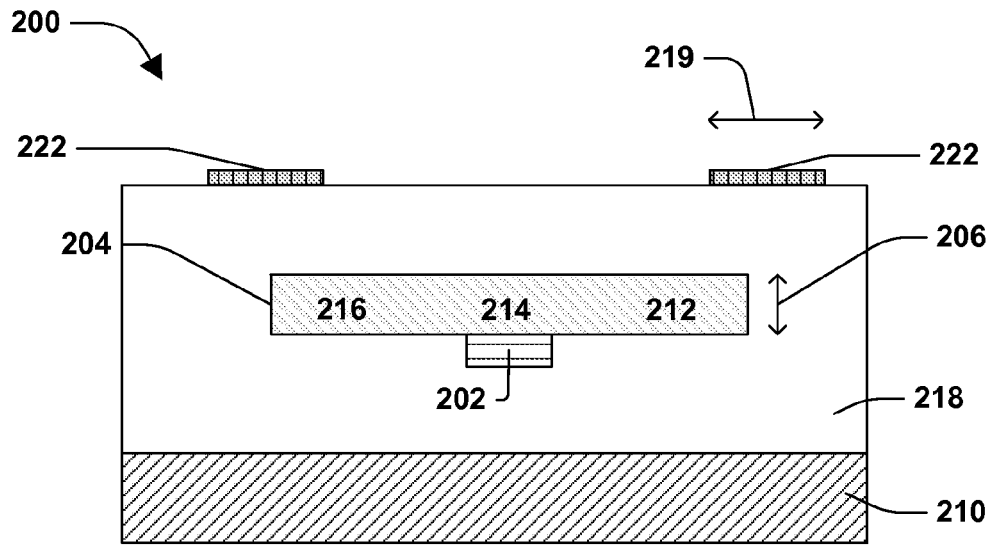
FIG. 4 is an illustration of a semiconductor device, according to some embodiments.

At 106, the conductive layer 220 is patterned to form a heating element 222, as illustrated in FIG. 4. In some embodiments, the heating element comprises a width 219 of between about 0.05 μm to about 5 μm. In some embodiments, there are multiple heating elements 222. In some embodiments, the heating element 222 is above the active region 204. In some embodiments, one heating element is generally situated above the source 212 while another heating element is generally situated above the drain 216.

Figure 5:
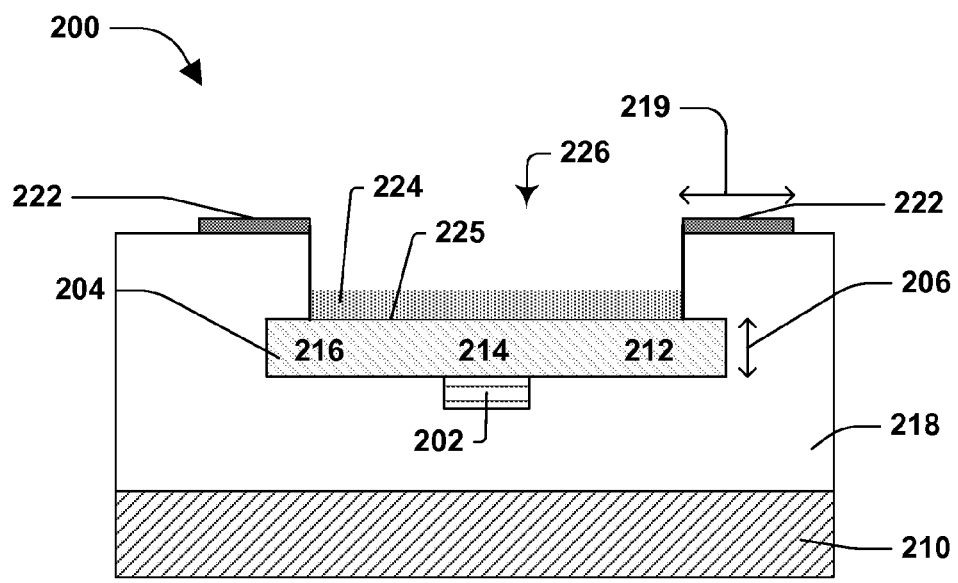
FIG. 5 is an illustration of a semiconductor device, according to some embodiments.

At 108, a first opening 226 is formed in the dielectric layer 218, as illustrated in FIG. 5. The first opening 226 is over the active region 204. In some embodiments, the first opening 226 descends to an active region surface 225. In some embodiments, the first opening comprises a cubic volume of between about 0.01 μm$^3$ to about 150 μm$^3$. In some embodiments, the first opening 226 is formed by etching the dielectric layer 218, where unetched portions of the semiconductor device 200 are masked off during the etching of the dielectric layer 218.

At 110, an ion sensing film 224 is formed in the first opening 226, as illustrated in FIG. 5. In some embodiments, the ion sensing film 224 comprises at least one of hafnium oxide (HfO$_2$), SiO$_2$, or tantalum pentoxide (Ta$_2$O$_5$). In some embodiments, the ion sensing film 224 is applied using thermal deposition. In some embodiments, the ion sensing film 224 is in direct contact with the active region surface 225.

Figure 6:
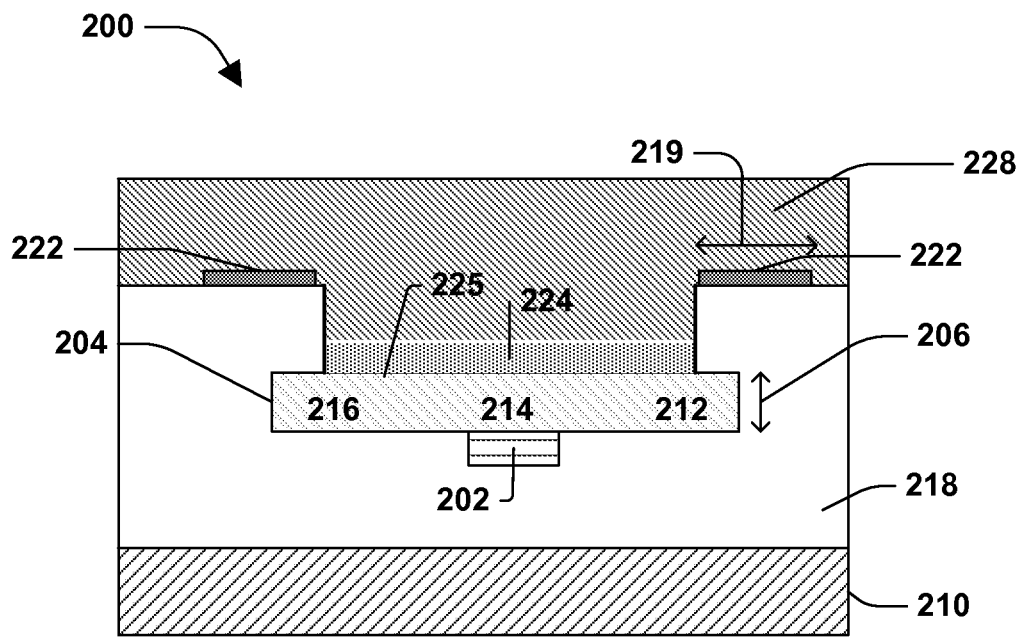
FIG. 6 is an illustration of a semiconductor device, according to some embodiments.

At 112, a passivation layer 228 is formed over the ion sensing film 224, the heating element 222, and the exposed dielectric layer 218, as illustrated in FIG. 6. In some embodiments, the passivation layer 228 comprises at least one of SiO$_2$ or silicon nitride (Si$_3$N$_4$). In some embodiments, the passivation layer 228 comprises a thickness of between about 0.1 μm to about 5 μm.

Figure 7:
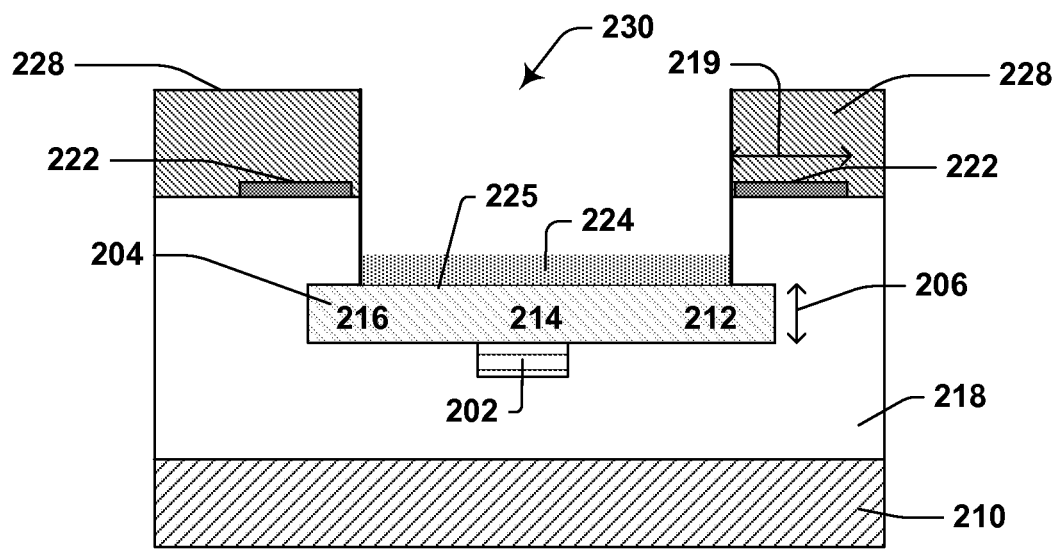
FIG. 7 is an illustration of a semiconductor device, according to some embodiments.

At 114, a second opening 230 is formed in the passivation layer 228, as illustrated in FIG. 7. In some embodiments, the second opening 230 descends down to the ion sensing film 224. In some embodiments, the passivation layer 228 is thin etched away from the ion sensing film 224.

Figure 8:
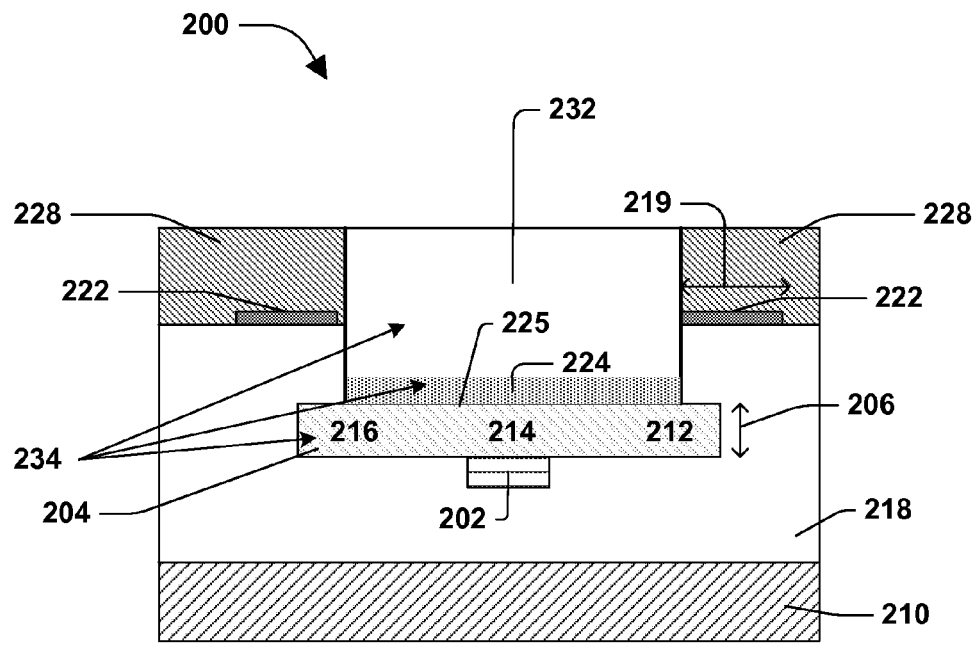
FIG. 8 is an illustration of a semiconductor device, according to some embodiments.

At 116, an ion sensing region 232 is formed, as illustrated in FIG. 8. In some embodiments, the ion sensing region 232 comprises a bio-solution. In some embodiments, the bio-solution is injected into the ion sensing region 232 by molecular injection. In some embodiments, the ion sensing region 232 comprises a cubic volume of between about 0.01 μm$^3$ to about 150 μm$^3$. In some embodiments, the ion sensing device 234 comprises the action region 204, the ion sensing film 224 and the ion sensing region 232. The ion sensing device 234 is configured to detect a change in a charge of the bio-solution that results from a reaction in the ion sensing region 232. In some embodiments, DNA replication alters the bio-solution charge such that current will or will not flow through the channel 214 between the source 212 and the drain 216 depending upon, among other things, a magnitude of the change to the charge of the bio-solution, a composition of the active region 204 and the ion sensing film 224, and a temperature of the ion sensing device 234, which is affected by selective activation of the heating element 222. In some embodiments, DNA replication in the bio-solution is promoted by switching a temperature of the ion sensing region 232 between at least one of first, second or third temperatures, where selective activation of the heating element effects such switching.

Figure 9:
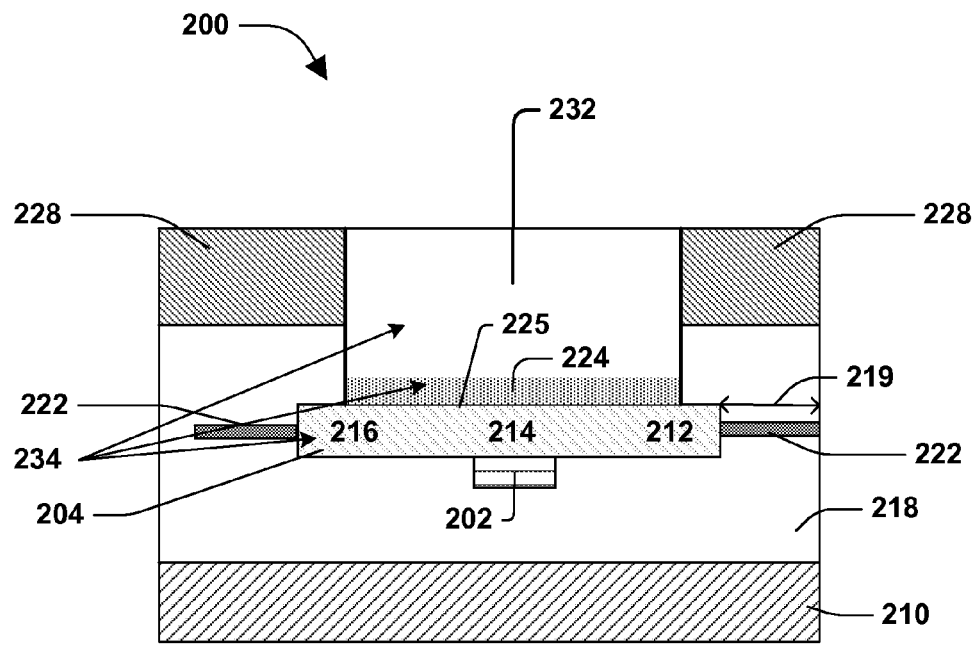
FIG. 9 is an illustration of a semiconductor device, according to some embodiments.

FIG. 9 is an illustration of the semiconductor device 200 where the heating element 222 is in line or substantially co-planar with the activation region 204, according to some embodiments. In some embodiments, the heating element 222 is formed during formation of the active region. In some embodiments, to form the heating element 222 at this locale, an opening is formed, such as by etching, into a material or layer within which the action region 204 is formed, such as a thermal electric isolation layer. The opening is then filled, such as by deposition, with a material for the heating element, such as a metal. In some embodiments, the heating element 222 touches at least one side of the active region 234. In some embodiments, the heating element 222 is adjacent, but does not touch the active region 234.

Figure 10:
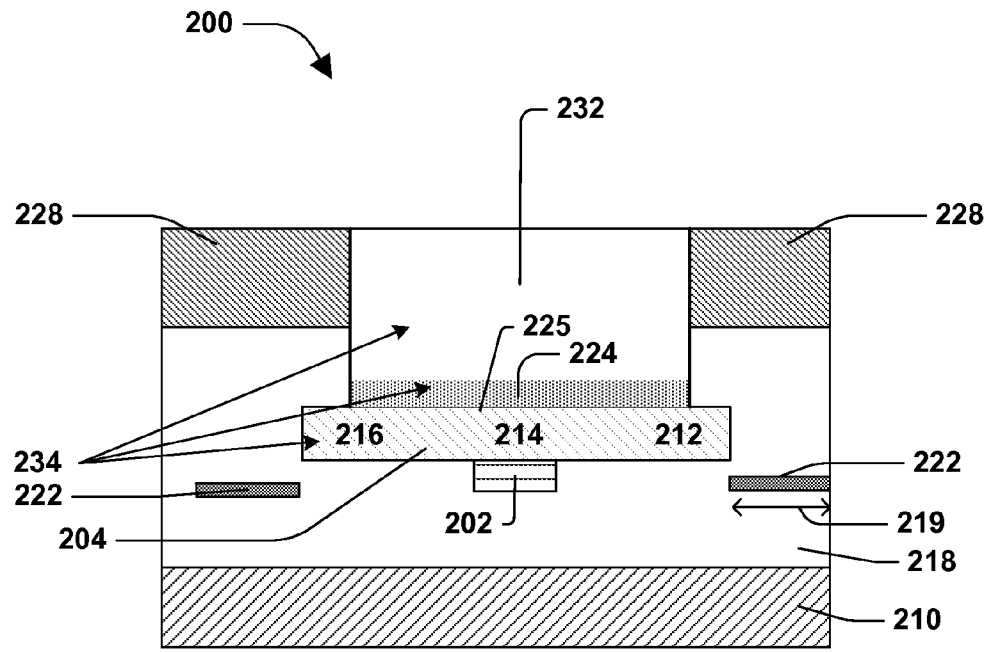
FIG. 10 is an illustration of a semiconductor device, according to some embodiments.

FIG. 10 is an illustration of the semiconductor device 200 where the heating element 222 is below the active region 204, according to some embodiments. In some embodiments, the heating element 222 is formed prior to formation of the active region 234. In some embodiments, to form the heating element 222 at this locale, an opening is formed, such as by etching, into the dielectric layer 218. The opening is then filled, such as by deposition, with a material for the heating element, such as a metal. In some embodiments, the heating element 222 is adjacent, but does not touch at least one side of the active region 204.

Figure 11:
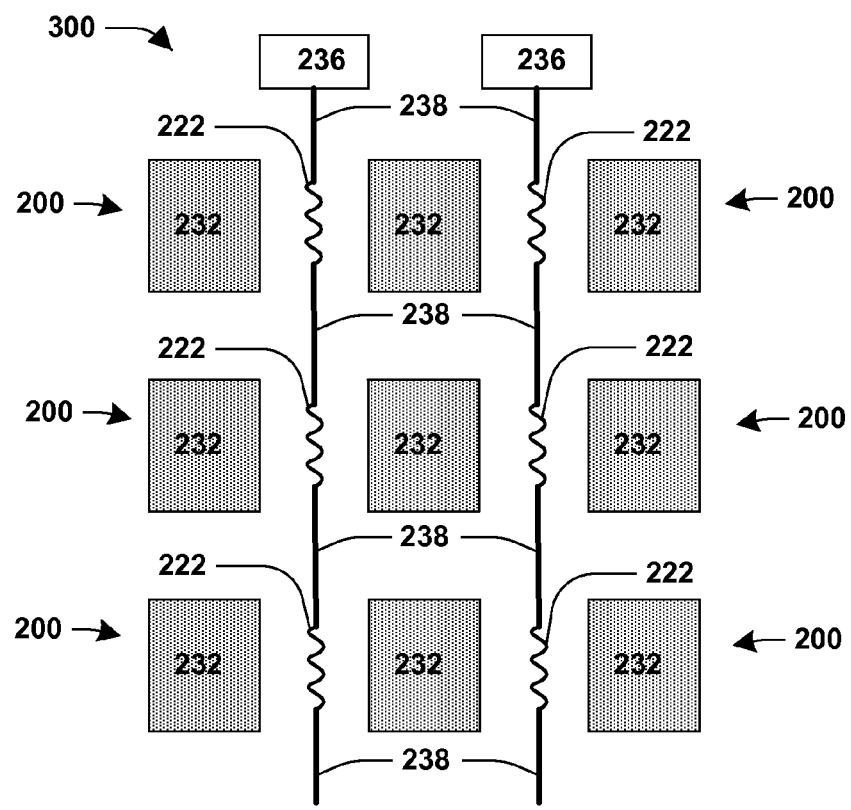
FIG. 11 is an illustration of an array, according to some embodiments.

FIG. 11 is a top view of an array 300, according to some embodiments. The array 300 comprises a plurality of semiconductor devices 200 arranged in a grid-like pattern with heating elements 222 disposed between semiconductor devices 200. A power source 236 is connected to conductive lines 238 within which the heating elements 222 are comprised. In some embodiments, a single power source 236 is implemented, such as where the heating elements are connected in series. In some embodiments, multiple power sources are implemented, where respective power supplies cause current to flow within some but fewer than all heating elements 222. In some embodiments, an ion sensing device 234 is surrounded by multiple heating elements 222. In some embodiments, four heating elements 222 surround an ion sensing device 234, such as a heating element 222 to the left, right, top and bottom of the ion sensing device 234. In some embodiments, heating elements 222 are arranged to form a ring, oval, square or other shape around an ion sensing device 234. In some embodiments, a first configuration of heating elements 222, such as a circular arrangement, is formed around a first ion sensing device 234 while a second configuration of heating elements 222, such as square arrangement, is formed around a second ion sensing device 234.

Figure 12:
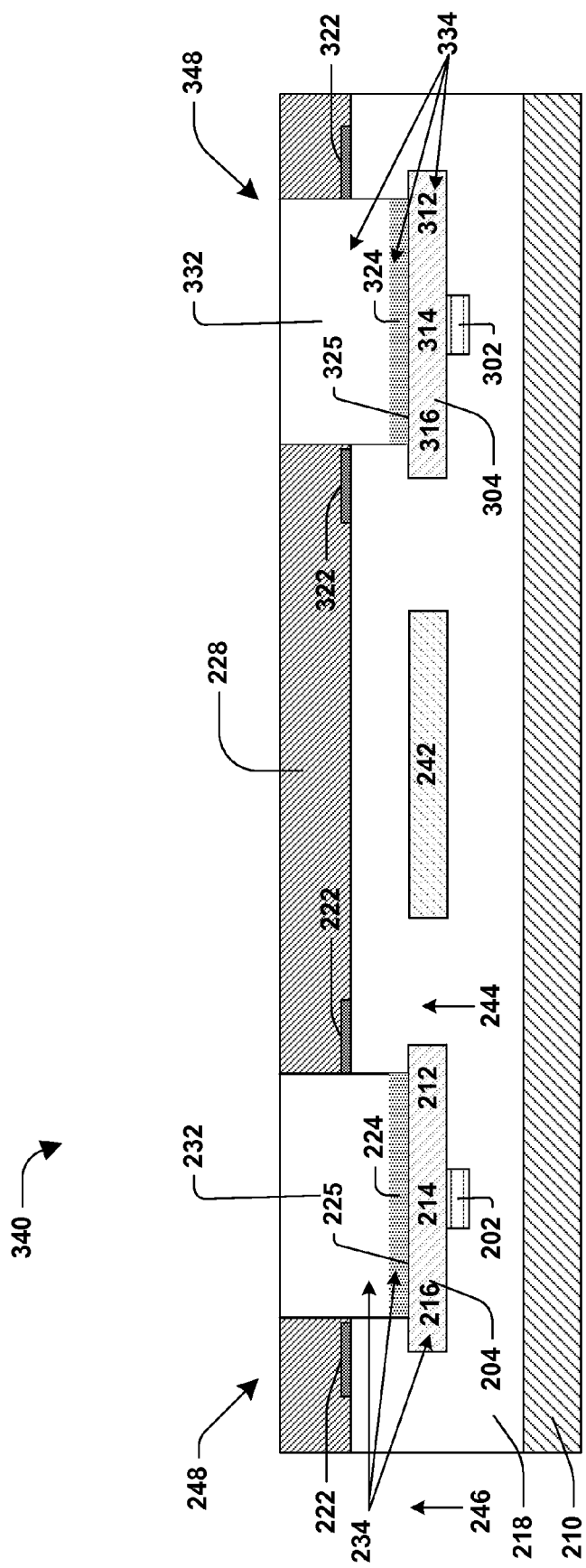
FIG. 12 is an illustration of an array, according to some embodiments.

FIG. 12 is an illustration of an array 340, according to some embodiments. The array 340 comprises multiple adjacent semiconductor devices, such as a first semiconductor device 248 and a second semiconductor device 348. In some embodiments, the first semiconductor device 248 and the second semiconductor device 348 are formed in a common set of layers. In some embodiments, the first semiconductor device 248 and the second semiconductor device 348 are formed concurrently, such as using the method 100 described with respect to FIG. 1. In some embodiments, a thermal sensor 242 is situated to a first side 244 of the first semiconductor device 248. In some embodiments, a second thermal device (not shown) is situated to a second side 246 of the first semiconductor device 248. In some embodiments, the thermal sensor 242 is formed within the dielectric layer 218 and is substantially co-planar with the active region 204 of the first semiconductor device 248. In some embodiments, the thermal sensor 242 comprises a thickness of between about 0.01 µm to about 5 µm. In some embodiments, the thermal sensor 242 comprises one of a thermal diode, a diode connected FET or MOSFET, or thermal resistance.

In some embodiments, the second semiconductor device 348 comprises a second ion sensing device 334. In some embodiments, the second ion sensing device 334 comprises a second active region 304, a second ion sensing film 324 on the active region surface 325, and a second ion sensing region 332. In some embodiments, the second active region 304 comprises a second source 312, a second drain 316, and a second channel 314. In some embodiments, the second channel 314 is situated between the second source 312 and second drain 316, and above a second gate 302. In some embodiments, the second gate 302 is adjacent the second active region 304 diametrically opposite a second ion sensing film 324 relative to the second channel 314. In some embodiments, the second semiconductor device 348 comprises a second heating element 322 proximate the second ion sensing device 334. In some embodiments, the thermal sensor 242 is configured to sense a local temperature, and thus a temperature substantially equal to at least one of a temperature of the first semiconductor device 248 or a temperature of the second semiconductor device 348. The thermal sensor 242 is configured to communicate with at least one of the heating element 222 or the second heating element 322, such as through a conductive trace (not shown), to alter at least one of a temperature of the ion sensing region 232 or a temperature of the second ion sensing region 332, such as to facilitate DNA replication to promote desired operation of at least one of the first semiconductor device 248 or the second semiconductor device 348, such as to function as a bio sensor.

In some embodiments, a semiconductor device comprises an ion sensing device. In some embodiments, the ion sensing device comprises a source, a drain and a channel situated between the source and the drain. In some embodiments, an ion sensing film is situated over the channel. In some embodiments, an ion sensing region is situated over the ion sensing film. In some embodiments, a heating element is proximate the ion sensing device.

In some embodiments, a method of forming a semiconductor device comprises forming an ion sensing device and forming a heating element proximate the ion sensing device.

In some embodiments, an array comprises a first ion sensing device. In some embodiments, the array comprises a first heating element proximate the first ion sensing device. In some embodiments, the array comprises a second ion sensing device. In some embodiments, the array comprises a second heating element proximate the second ion sensing device.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated having the benefit of this description. Further, it will be understood that not all operations are necessarily present in each embodiment provided herein. Also, it will be understood that not all operations are necessary in some embodiments.

It will be appreciated that layers, features, elements, etc. depicted herein are illustrated with particular dimensions relative to one another, such as structural dimensions or orientations, for example, for purposes of simplicity and ease of understanding and that actual dimensions of the same differ substantially from that illustrated herein, in some embodiments. Additionally, a variety of techniques exist for forming the layers features, elements, etc. mentioned herein, such as etching techniques, implanting techniques, doping techniques, spin-on techniques, sputtering techniques such as magnetron or ion beam sputtering, growth techniques, such as thermal growth or deposition techniques such as chemical vapor deposition (CVD), physical vapor deposition (PVD), plasma enhanced chemical vapor deposition (PECVD), or atomic layer deposition (ALD), for example.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application and the appended claims are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used, such terms are intended to be inclusive in a manner similar to the term "comprising". Also, unless specified otherwise, "first," "second," or the like are not intended to imply a temporal aspect, a spatial aspect, an ordering, etc. Rather, such terms are merely used as identifiers, names, etc. for features, elements, items, etc. For example, a first region and a second region generally correspond to region A and region B or two different or two identical regions or the same region.

Also, although the disclosure has been shown and described with respect to one or more implementations, equivalent alterations and modifications will occur to others skilled in the art based upon a reading and understanding of this specification and the annexed drawings. The disclosure comprises all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A semiconductor device, comprising:
   an ion sensing device, comprising:
   an active region comprising a source, a drain and a channel situated between the source and the drain;
   a gate situated over a first surface of the active region;
   an ion sensing film situated over a second surface of the active region diametrically opposing the first surface; and
   an ion sensing region situated over the ion sensing film, wherein the active region and the gate are embedded within a dielectric layer; and
   a heating element proximate the ion sensing device.

2. The semiconductor device of claim 1, comprising:
   a thermal sensor proximate at least one of the ion sensing device or the heating element.

3. The semiconductor device of claim 1, comprising a conductive line connected to the heating element and configured to apply a current to the heating element.

4. The semiconductor device of claim 1, the heating element in contact with a surface of the dielectric layer.

5. The semiconductor device of claim 1, the ion sensing device comprising an ion sensing field effective transistor, a nanowire, or a MOSFET.

6. The semiconductor device of claim 1, the heating element comprising a resistor.

7. The semiconductor device of claim 1, the heating element comprising at least one of metal or polysilicon.

8. The semiconductor device of claim 1, the ion sensing region comprising a bio-solution.

9. The semiconductor device of claim 1, the ion sensing region comprising a cubic dimension of between about 0.5 $\mu m^3$ to about 1.5 $\mu m^3$.

10. The semiconductor device of claim 1, the ion sensing film comprising at least one of $HfO_2$, $Ta_2O_5$, or $SiO_2$.

11. The semiconductor device of claim 1, wherein the ion sensing region caps the ion sensing film.

12. The semiconductor device of claim 1, wherein the heating element is not in contact with the active region.

13. A method of forming a semiconductor device comprising:
   acquiring a composite structure comprising a dielectric layer and a field effect transistor (FET) embedded within the dielectric layer;
   forming a conductive layer on the dielectric layer, wherein an active region of the FET is disposed between a gate of the FET and a surface of the dielectric layer upon which the conductive layer is formed;
   patterning the conductive layer to define a heating element;
   etching the dielectric layer to form an opening that extends from the surface of the dielectric layer to the active region of the FET; and
   forming an ion sensing film within the opening.

14. The method of claim 13, comprising:
   forming a passivation layer over the heating element, the heating element in contact with the dielectric layer and the passivation layer.

15. The method of claim 14, comprising:
   forming a second opening in the passivation layer over the ion sensing film; and
   forming an ion sensing region of an ion sensing device within the second opening.

16. An array, comprising:
   a first ion sensing device;
   a first heating element proximate the first ion sensing device;
   a second ion sensing device;
   a second heating element proximate the second ion sensing device; and
   a thermal sensor situated between the first ion sensing device and the second ion sensing device.

17. The array of claim 16, the first ion sensing device, comprising;
   a first active region comprising a first source, a first drain, and a first channel situated between the first source and the first drain;
   a first ion sensing film situated over the first channel; and
   a first ion sensing region situated over the first ion sensing film.

18. The array of claim 17, the second ion sensing device, comprising:
   a second active region comprising a second source, a second drain, and a second channel situated between the second source and the second drain;
   a second ion sensing film situated over the second channel; and
   a second ion sensing region situated over the second ion sensing film.

19. The array of claim 16, at least one of the first heating element or the second heating element comprising a resistor.

20. The array of claim 16, the thermal sensor configured to cause at least one of a first current to flow through the first heating element at a first time to promote a first temperature at the first ion sensing device, a second current to flow through the first heating element at a second time to promote a second temperature at the first ion sensing device, or a third current to flow through the first heating element at a third time to promote a third temperature at the first ion sensing device.

* * * * *